United States Patent
Kawahara et al.

(10) Patent No.: US 6,914,151 B1
(45) Date of Patent: Jul. 5, 2005

(54) CRYSTALLIZATION PROCESSES FOR THE FORMATION OF STABLE CRYSTALS OF ASPARTAME DERIVATIVE

(75) Inventors: Shigeru Kawahara, Kawasaki (JP); Akihiro Kishishita, Kawasaki (JP); Kazutaka Nagashima, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/830,159

(22) PCT Filed: Nov. 1, 1999

(86) PCT No.: PCT/JP99/06082

§ 371 (c)(1),
(2), (4) Date: Jun. 27, 2001

(87) PCT Pub. No.: WO00/26234

PCT Pub. Date: May 11, 2000

(30) Foreign Application Priority Data

Oct. 30, 1998 (JP) .......................................... 10/310225
Oct. 30, 1998 (JP) .......................................... 10/310226

(51) Int. Cl.$^7$ .......................................... C07C 229/00
(52) U.S. Cl. ....................................................... 560/40
(58) Field of Search ..................................... 560/40, 41

(56) References Cited

U.S. PATENT DOCUMENTS

| 4,579,747 | A |   | 4/1986 | Sugiyama et al. |
| 4,950,780 | A |   | 8/1990 | Tanaka et al. |
| 5,510,508 | A | * | 4/1996 | Claude et al. |
| 5,728,862 | A |   | 3/1998 | Prakash |
| 6,316,657 | B1 |  | 11/2001 | Takemoto |
| 6,335,461 | B1 |  | 1/2002 | Amino et al. |
| 6,346,642 | B1 |  | 2/2002 | Kishishita et al. |
| 6,372,278 | B1 |  | 4/2002 | Ishida et al. |
| 6,372,279 | B1 |  | 4/2002 | Ishida et al. |
| 6,399,132 | B1 |  | 6/2002 | Ishida et al. |
| 6,444,251 | B1 |  | 9/2002 | Kishishita et al. |
| 6,613,933 | B1 |  | 9/2003 | Nagashima et al. |
| 6,673,838 | B2 |  | 1/2004 | Hadfield et al. |
| 6,706,304 | B1 |  | 3/2004 | Ishida et al. |

FOREIGN PATENT DOCUMENTS

| EP | 0 279 542 | 8/1988 |
| EP | 0 514 939 | 11/1992 |
| WO | WO 93/02101 | 2/1993 |
| WO | WO 95/30688 | 11/1995 |
| WO | WO 95/30689 | 11/1995 |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A crystallization process for forming a stable crystal of N-(3,3-dimethylbutyl)-APM, which comprises using either water or a mixture of water with a lower alcohol as the crystallizing solvent and controlling the crystallization point to 30° C. or above; and another crystallization process therefor, which comprises using either water or a mixture of water with a lower alcohol as the crystallizing solvent and using as the seed crystal a crystal of N-(3,3-dimethylbutyl)-APM exhibiting peculiar peaks of diffracted X-ray at least at diffraction angles (2θ, CuKα ray) of 6.0°, 24.8°, 8.2° and 16.5° to thereby crystallize the above objective crystal preferentially. These crystallization processes enable the constant formation of stable crystals of N-(3,3-dimethylbutyl)-APM at a low cost.

16 Claims, 4 Drawing Sheets

CRYSTALLIZATION PROCESSES FOR THE FORMATION OF STABLE CRYSTALS OF ASPARTAME DERIVATIVE

This application is a 371 of PCT/JP99/06082 filed on Nov. 1, 1999, which claims the benefit of JP 310225 and JP 310226 both filed on Oct. 30, 1998.

TECHNICAL FIELD

The present invention relates to a process for preparing the highly stable crystals of N-[N-(3,3-dimethylbutyl)-L-α-aspartyl]-L-phenylalanine methyl ester, which is a high intensity sweetener. L-α-aspartyl-L-phenylalanine methyl ester is, as is well known, one of amino acid type high intensity sweeteners which has already been commercialized, and it is abbreviated as APM or aspartame. The sweetener relating to the present invention is therefore considered as an APM or aspartame derivative, and will hereinafter be abbreviated as N-(3,3-dimethylbutyl)-APM. Additionally, this sweetener is abbreviated as Neotame in some publications.

BACKGROUND ART

N-(3,3-dimethylbutyl)-ATM has a sweetening potency, on the weight basis, of at least 50 times that of aspartame and about 10,000 times that of sucrose (table sugar) so that it can constitute a high intensity sweetener.

Since sweetening agents are mainly employed in foods for human consumption, they must be prepared using a method which can provide a highly purified product substantially free from impurities or decomposition products. Furthermore, in the case of a sweetening substance which tends to be decomposed relatively easily, like N-(3,3-dimethylbutyl)-APM, some countermeasures are required against the decomposition thereof after forwarded as a product.

The already known crystals of N-(3,3-dimethylbutyl)-APM are described in WO95/30689 with reference to the IR spectrum data. The present inventors have confirmed that these crystals are monohydrate crystals as a result of the X-ray crystal structure analysis, and that they show the specific peaks of diffracted X-rays at angles of diffraction of at least 6.0°, 24.8°, 8.2° and 16.5° when measured by a powder X-ray diffractometer using CuKα radiation. The present inventors have decided to call these crystals "A-type crystal" for convenience' sake.

Meanwhile, a preparation process of N-(3,3-dimethylbutyl)-APM is also described in U.S. Pat. No. 5,278,862, wherein high purity (97% by HPLC) N-(3,3-dimethylbutyl)-APM is obtained by crystallization using methanol and water as the crystallization solvent.

Figure 1:
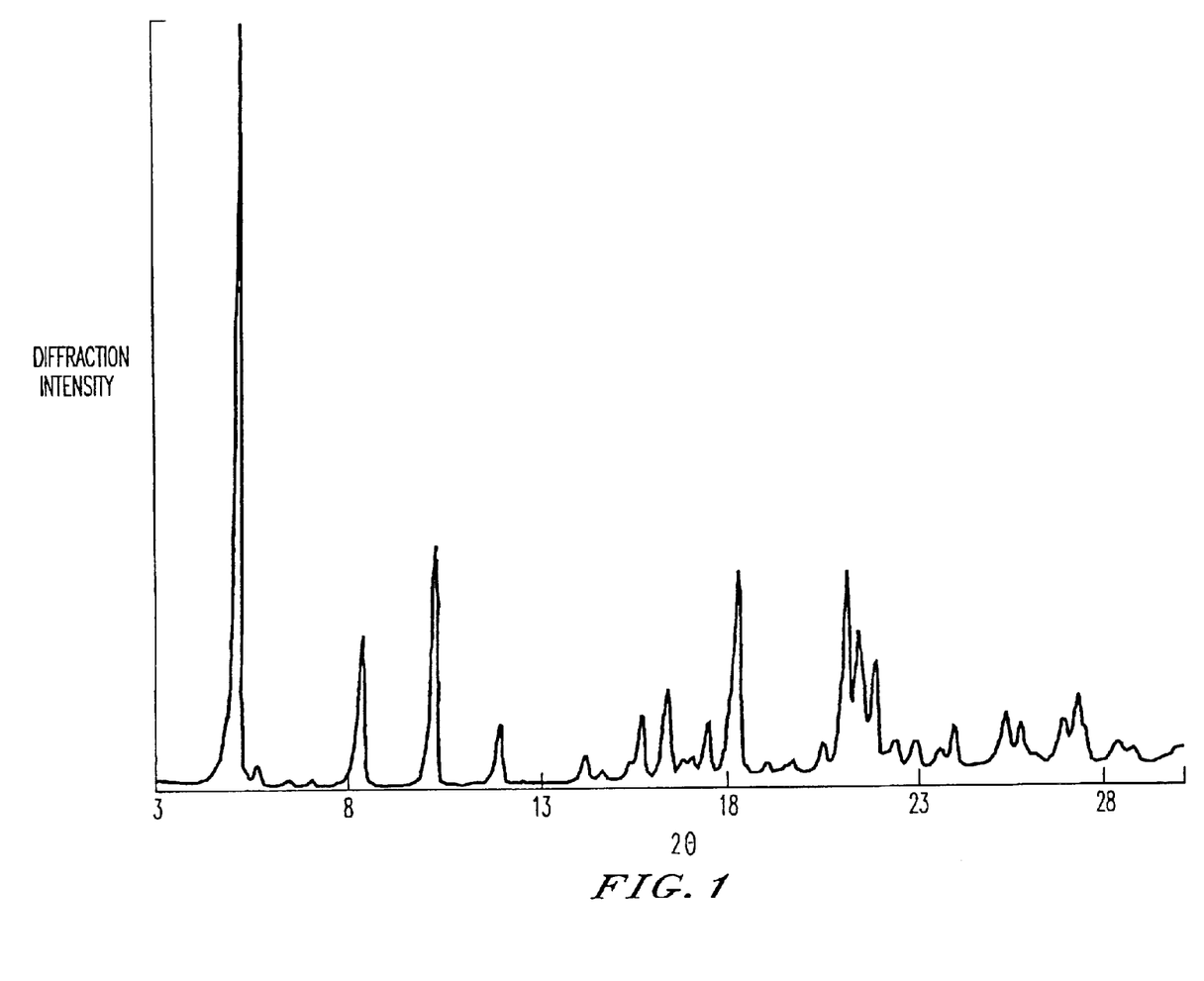
FIG. 1 shows a powder X-ray diffraction pattern of the B-type crystals.

And, the present inventors have followed Example 1 of the said U.S. Pat. No. 5,278,862. As the results, although they have confirmed the reproducibility of the data on purity (98% by HPLC), they could not confirm the formation of A-type crystals. In greater detail, the resulting crystals showed, as wet crystals, the specific peaks of diffracted X-rays at angles of diffraction (2θ, CuKα rays) of at least 5.10, 21.10, 21.3° and 8.3°. The powder X-ray diffraction pattern at this time will be given in FIG. 1. These crystals will hereinafter be called "B-type crystal".

Figure 2:
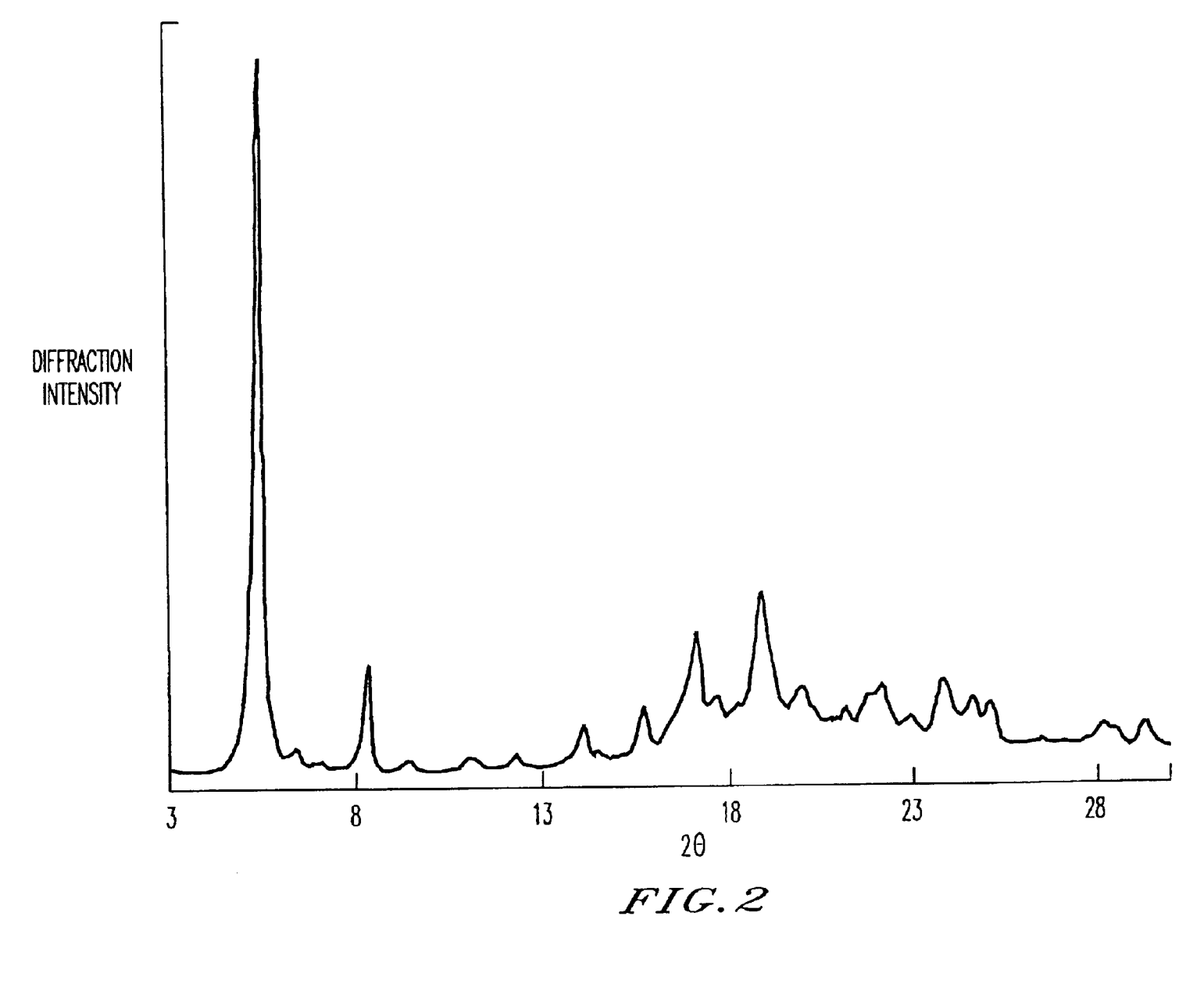
FIG. 2 shows a powder X-ray diffraction pattern of the G-type crystals.

Furthermore, the B-type crystals obtained by following Example 1 of the said U.S. Pat. No. 5,728,862, when dried, gave crystals exhibiting the specific peaks of diffracted X-rays at angles of diffraction (2θ, CuKα rays) of at least 5.6°, 8.4°, 17.1° and 18.8°. The powder X-ray diffraction pattern at this time will be given in FIG. 2. As a result of measurement by Karl Fisher's method, the water content of these crystals were found to be 0.6 wt. %. These crystals will hereinafter be called "G-type crystal".

The resulting G-type crystals and A-type crystals of N-(3,3-dimethylbutyl)-APM were tested at 70° C., concerning their stability. As a result, after the lapse of 160 hours, the remaining ratio of the N-(3,3-dimethylbutyl)-APM in the form of the G-type crystals was 34 wt. %, while that in the form of the A-type crystals was 94 wt. %, suggesting that N-(3,3-dimethylbutyl)-APM is more stable in the form of A-type crystals. The relationship between the storage time and the remaining ratio of N-(3,3-dimethylbutyl)-APM in this test will be shown below in Table 1.

TABLE 1

Stability test at 70° C.

| Crystal type | Time elapsed (hrs) | | |
| --- | --- | --- | --- |
| | 0 Remaining ratio (wt. %) | 52 Remaining ratio (wt. %) | 160 Remaining ratio (wt. %) |
| A | 95 | 95 | 94 |
| G | 96 | 87 | 34 |

As described above, it has been found that according to Example 1 of U.S. Pat. No. 5,728,862, G-type crystals of N-(3,3-dimethylbutyl)-APM which are inferior to A-type crystals in stability, are obtained.

(Disclosure of the Invention)

As has been described above, a process for stably preparing A-type crystals excellent in stability, of N-(3,3-dimethylbutyl)-APM at a low cost, has not yet been established in the existing state of art.

Therefore, it is an object of the present invention to provide a process for stably and conveniently preparing highly stable A-type crystals of N-(3,3-dimethylbutyl)-APM, which is a high intensity sweetener.

With a view to attaining the above-described object, the present inventors have carried out an extensive and intensive investigation. As a result, it has been found that, upon crystallization of N-(3,3-dimethylbutyl)-APM from a crystallization solvent consisting of water singly or a mixed solvent of water/alcohol, A-type crystals can be obtained stably as wet crystals by controlling the nucleation temperature, and the type of the crystals to be precipitated can be controlled to be A-type by using A-type crystals as seed crystals; and that dry A-type crystals can be obtained by drying these A-type crystals to have a water content of 3 to 6 wt. % (inclusive of the water of crystallization). Based on these findings, the present invention has been completed. It should be noted that the term "controlling the nucleation temperature" as used herein means "controlling so as to generate nucleation at 30° C. or greater".

Accordingly, the present invention relates, in a first aspect, to a crystallization method of N-[N-(3,3-dimethylbutyl)-L-α-aspartyl]-L-phenylalanine methyl ester crystals exhibiting the specific peaks of diffracted X-rays at angles of diffraction (2θ, CuKα rays) of at least 6.0°, 24.8 °, 8°, 8.2° and 16.5°, which comprises using water alone or a mixture of water and a lower alcohol as the crystallization solvent and controlling the nucleation temperature at 30° C. or greater, and in a second aspect, to a crystallization method of N-[N-(3,3-dimethylbutyl)-L-α-aspartyl)-L-phenylalanine methyl ester crystals, which comprises, using water alone or a mixture of water and a lower alcohol as the crystallization solvent and using, as the seed crystals, N-[N-(3,3-dimethylbutyl)-L-α-aspartyl]-L-phenylalanine methyl ester crystals exhibiting the specific peaks of diffracted X-rays at angles of diffraction (2θ, CuKα rays) of at least 6.0°, 24.8°, 8.2° and 16.5°, whereby the same type of crystals as the seed crystals are preferentially precipitated.

In the first place, the first-mentioned crystallization method will be described below.

Examples of the lower alcohol usable as a crystallization solvent according to the present crystallization method which belongs to a nucleation-point controlling method, include methanol, ethanol, isopropanol, and the like. Among them, methanol is more preferred because it can be supplied industrially at a low cost.

Although there are no particular limitations imposed on the methanol content in the crystallization system, the methanol content in the solution to be subjected to crystallization is preferably 15 wt. % or less because an excessively high methanol content disturbs smooth crystallization.

A-type crystals can be obtained by nucleation at 30° C. or greater. However, since high crystallization temperatures allow the decomposition of N-(3,3-dimethylbutyl)-APM to proceed, it is, in practice, preferred to generate nucleation at 30 to 65° C., more preferably 40 to 50° C. Concrete methods of such nucleation within the above-described range can be carried out, for example, (a) by maintaining a supersaturated solution of N-(3,3-dimethylbutyl)-APM at a temperature within the above-described range until nucleation occurs, (b) by cooling a saturated or supersaturated solution of N-(3,3-dimethylbutyl)-APM having a temperature of 30° C. or greater and generating nucleation before the temperature is lowered to 30° C., or the like. In such methods of nucleation, application of a mechanical impact such as supersonic or the like from the outside is effective for early nucleation. In short, it is easy for those who are skilled in the art to control the nucleation temperature by using, in appropriate combinations, factors such as concentration of N-(3,3-dimethylbutyl)-APM before beginning of crystallization, temperature, time, cooling rate, mechanical impact and the like.

When crystallization is started in the crystallization solvent system using water alone or a mixture of water/methanol, A-type crystals can be obtained, as has been described above, by controlling the nucleation temperature to be 30° C. or greater. By generating nucleation crystallization at a temperature lower than the above, however, A-type crystals are not formed but B-type crystals are formed as wet crystals. Such nucleation at such a lower temperature must therefore be avoided.

The present crystallization method can be conducted in accordance with the ordinary manners employed in the art as needed, except that the above-described solvent is employed for crystallization and the nucleation temperature is controlled to be 30° C. or greater.

It is needless to say that the present crystallization method can be effected in any one of crystallization operation manners such as batch crystallization, continuous crystallization, agitation crystallization, static crystallization, and the like.

It is well known that in any one of the above-described crystallization operation manners, the solubility of a substance to be crystallized is preferably lowered by using cooling crystallization (cooling operation) in combination in order to heighten the yield of crystals.

In the present crystallization method, it is of course possible to use cooling operation in combination. In greater detail, once A-type crystals are formed by adjusting the nucleation temperature to 30° C. or greater, the increased parts or the increment of the crystals resulting even after cooling of the crystallization system, is also A-type crystals because the already-formed A-type crystals serve as seed crystals. In the present crystallization method, no particular limitations are imposed on until what temperature the solution is cooled before separation of the crystals by filtration.

There are no particular limitations imposed on the apparatus for obtaining dry A-type crystals having a water content of 3 to 6 wt. % by drying the wet A-type crystals of N-(3,3-dimethylbutyl)-APM. A through-flow dryer, fluidized dryer, vacuum dryer, spray dryer, flash drying, pneumatic conveying dryer, or the like can be used freely.

In the next place, description will be made of the second-mentioned crystallization method.

Concerning crystallization, seeding crystallization means, in general, a method of crystallizing preferentially the same kind of crystals as the crystals seeded, by seeding with the crystals in a solution to be subjected to crystallization.

Examples of the lower alcohol usable as a crystallization solvent according to the present crystallization method which belongs to a seeding crystallization method, include methanol, ethanol, isopropanol, and the like. Among them, methanol is more preferred because it can be supplied industrially at a low cost. This is the same as what has been deseribed in connection with the first-mentioned crystallization method.

Although no particular limitations are imposed on the content of the lower alcohol in the solution to be subjected to crystallization, a content of 35 wt. % or less in the solution to be subjected to crystallization is preferred because too high alcohol concentrations disturb smooth precipitation of crystals. The alcohol concentration can be made higher according to this second-mentioned method compared with the first-mentioned crystallization method, because the addition of A-type crystals as seed crystals from the outside of the system makes it possible to omit adjustment of the nucleation temperature at 30° C. or greater.

According to the present seeding crystallization method, although no particular limitations are imposed on the temperature at which A-type crystals are added as seed crystals insofar as the solution is supersaturated at this temperature, preferred is 20° C. or greater, more preferably 25° C. or greater from the viewpoint of crystallizing operation easiness.

Although no particular limitations are imposed on the amount of A-type crystals to be added as seed crystals, preferred is 0.2 to 30% relative to the weight of the initial solute in the solution to be subjected to crystallization, because an excessively large amount deteriorates efficiency.

Although no particular limitations are imposed on the form of A-type crystals to be added as seed crystals, a solid or slurry is preferably added. Also recommended is use, as seed crystals, of the remaining slurry as such in a continuous crystallization.

The present crystallization method can be conducted in accordance with the ordinary manners as employed in the seeding crystallization method except for the above-described crystallization solvent and seed crystals.

It is needless to say that the present crystallization method can be effected in any one of crystallization operation manners such as batch crystallization, continuous crystallization, agitation crystallization, static crystallization, and the like.

In any one of the above-described crystallization operation manners, the solubility of a substance to be crystallized is preferably lowered by using cooling crystallization (cooling operation) in combination in order to heighten the yield of crystals, this being the same as has been described above in connection with the first-mentioned crystallization method.

Also, according to the present crystallization method, it is of course possible to use cooling operation in combination. No particular limitations are imposed on until what temperature the solution is cooled before separation of the crystals by filtration.

There are no particular limitations imposed on the apparatus for obtaining dry A-type crystals having a water content of 3 to 6 wt. % by drying the wet A-type crystals of N-(3,3-dimethylbutyl)-APM. As has been described above in connection with the first-mentioned crystallization method, a through-flow dryer, fluidized dryer, vacuum dryer, spray dryer, flash dryer, pneumatic conveying dryer or the like can be widely used.

BEST MODE FOR CARRYING OUT THE INVENTION

The present invention will hereinafter be described more specifically with reference to Examples.

In the first place, Examples of the first-mentioned crystallization method will be described.

EXAMPLE 1

Preparation of A-type Crystals of N-(3,3-dimethylbutyl)-APM

In a reactor being equipped with an agitating blade and permitting markedly smooth transfer of gaseous hydrogen into the liquid layer, the following substances were charged with stirring: 550 mL of ion-exchanged water, 1100 mL of methanol, 61 g of aspartame, 20 g of 10% palladium-carbon (having a water content of 50 wt. %) and 19 g of 3,3-dimethylbutyl aldehyde.

After the completion of charging, hydrogen gas was introduced at a flow rate of 200 mL/min while the mixture was continued to be stirred at room temperature. The progress of the reaction was monitored by sampling the reaction mixture and analyzing the resulting products in the samplers by high-performance liquid chromatography (HPLC). After six hours' reaction, the reactor was filled with a nitrogen gas stream, followed by filtration through a microporous filter (0.50 μm) to remove the catalyst. The filtrate (1,460 g), when analyzed, revealed that the N-(3,3-dimethylbutyl)-APM had been produced in an amount of 64 g (yield: 85%).

The filtrate was then concentrated to 497 g, whereby crystals were precipitated. The resulting slurry was heated at 70° C. to dissolve the crystals. Then, the resulting solution was analyzed by gas chromatography, and revealed that the methanol content in the solution was 8.15 wt. %.

Subsequently, this uniform solution of N-(3,3-dimethylbutyl)-APM was gradually cooled from 70° C. to 40° C. and maintained at 40° C. for 1 hour, whereby nucleation was generated spontaneously.

Next, the resulting slurry was then cooled to 5° C. at a cooling rate of 5° C./hour, and aged overnight at this temperature, followed by separating the crystals by filtration.

Figure 3:
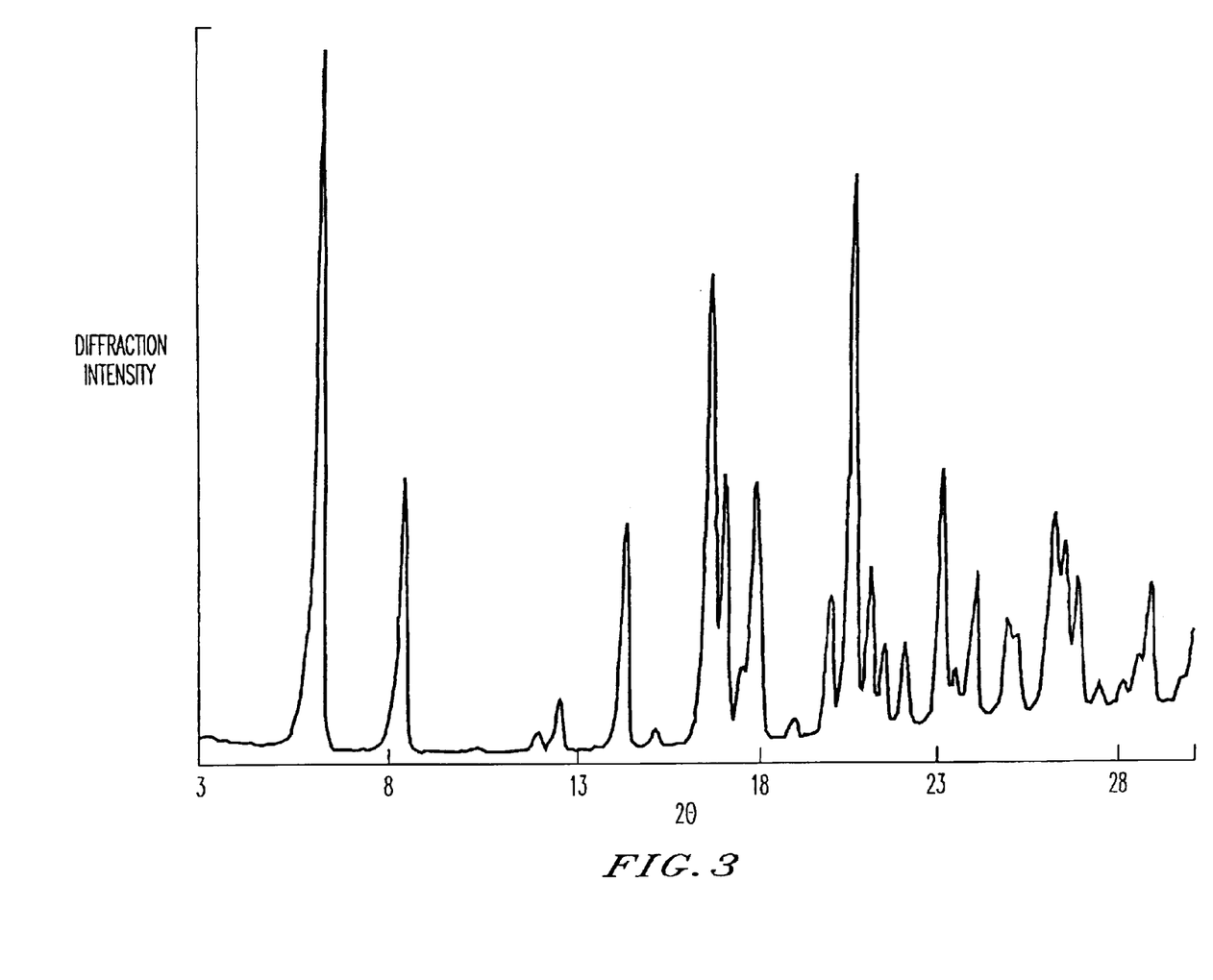
FIG. 3 shows a powder X-ray diffraction pattern of the wet A-type crystals (See Example 1)

As a result of measuring the diffracted X-rays by using CuKα rays in accordance with the powder X-ray diffraction method, the wet crystals thus separated showed the specific peaks of diffracted X-rays at angles of diffraction (2θ, CuKα rays) of at least 6.0°, 24.8°, 8.2° and 16.5°, indicating that the resulting crystals were A-type crystals. The powder X-ray diffraction pattern at this time will be shown in FIG. 3. And, the water content of the crystals was found to be 51.14 wt. % as measured directly by the Karl Fisher's method.

The above-described wet crystal's were then dried at 50° C. under reduced pressure until the water content became 5.8 wt. %, whereby 58 g of N-(3,3-dimethylbutyl)-APM was obtained (yield: 72%, and a purity of 97% by HPLC). As a result of measuring the diffracted X-rays in accordance with the powder X-ray diffraction method, the dried crystals showed the specific peaks of diffracted X-rays at angles of diffraction (2θ, CuKα rays) of at least 6.0°, 24.8°, 8.2° and 16.5°, indicating that the resulting dry crystals were also A-type crystals. The powder X-ray diffraction pattern at this time will be shown in FIG. 4. The IR spectrum data of these crystals were completely identical to those described in WO95/30689.

EXAMPLE 2

Crystallization from a Methanol/water Mixed Solvent (Nucleation temperature: 47° C.)

Into a three-necked flask, 5.0 g of N-(3,3-dimethylbutyl)-APM, 1.9 g of methanol and 30.9 g of water were weighed. The mixture was heated to 70° C. to completely dissolve the crystals in the solvent, whereby a solution having a methanol content of 5 wt. % in the whole solution was prepared. Subsequently, the flask having the resulting solution therein was dipped in a water bath of 47° C. for 1 hour. When the temperature of the solution in the flask became 47° C., nucleation occurred spontaneously. After the crystals were aged for 2 hours at the same temperature, the crystals were collected by filtration.

The diffracted X-rays of the wet crystals thus collected were measured using CuKα rays in accordance with the powder X-ray diffraction method. As a result, the wet crystals were found to be A-type crystals. The wet crystals were then subjected to the same operation as in Example 1, whereby dry A-type crystals were obtained.

EXAMPLE 3

Crystallization from a Methanol/water Mixed Solvent (Nucleation Temperature: 40° C.)

In the same manner as in Example 2, 2.0 g of N-(3,3-dimethylbutyl)-APM, 2.1 g of methanol and 37.4 g of water were charged into a three-necked flask. The mixture was heated to 70° C. to completely dissolve the crystals in the solvent, whereby a solution having a methanol content of 5 wt. % in the whole solution was prepared. Subsequently, the flask having the resulting solution therein was dipped in a water bath of 40° C. When the temperature of the solution in the flask became 40° C., nucleation occurred spontaneously. After the crystals were aged for 1 hour at the same temperature, the resulting crystals were collected by filtration.

The diffracted X-rays of the wet crystals thus collected were measured using CuKα rays in accordance with the powder X-ray diffraction method. As a result, the wet crystals were found to be A-type crystals. The wet crystals were then subjected to the same operation as in Example 1, whereby dry A-type crystals were obtained.

EXAMPLE 4

Crystallization from an Aqueous Solution
(Nucleation Temperature: 48° C.)

Into a three-necked flask, N-(3,3-dimethylbutyl)-APM and water were charged to prepare a slurry of N-(3,3-dimethylbutyl)-APM having a concentration of 5 g/dL in terms of the concentration in the homogeneous system. The resulting slurry was heated to 70° C. to completely dissolve the crystals. Subsequently, the flask having the resulting solution therein was dipped in a water bath of 50° C. When the temperature of the solution in the flask became 48° C., nucleation occurred spontaneously. After the crystals were aged for 2 hours at the same temperature, the resulting crystals were collected by filtration.

The diffracted X-rays of the wet crystals thus collected were measured using CuKα rays in accordance with the powder X-ray diffraction method. As a result, the wet crystals were found to be A-type crystals. The wet crystals were then subjected to the same operation as in Example 1, whereby dry A-type crystals were obtained.

COMPARATIVE EXAMPLE 1

Crystallization from a Methanol/water Mixed Solvent (Nucleation Temperature: 13° C.)

Into a three-necked flask, 13 g of N-(3,3-dimethylbutyl)-APM, 31 g of methanol and 96 g of water were weighed. The resulting mixture was heated to 50° C. to dissolve the crystals completely in the solvent, whereby a solution having a methanol content of 22 wt. % in terms of the concentration in the whole solution was prepared. Subsequently, the flask having the resulting solution therein was dipped in a water bath of 5° C. for 1 hour. When the temperature of the solution became 13° C., nucleation occurred spontaneously. After the crystals were aged for 2 hours at the same temperature, the resulting crystals were collected by filtration.

The diffracted X-rays of the wet crystals thus collected were measured using CuKα rays in accordance with the powder X-ray diffraction method. As a result, the wet crystals were found to be B-type crystals.

Refer to Comparative Examples 2 and 3 which will be described later.

In the next place, description will be made of Examples of the second-mentioned crystallization method.

EXAMPLE 5

Seeding or Implanting Seed Crystals at 28° C.

Into a three-necked flask, 22 g of N-(3,3-dimethylbutyl)-APM obtained in the same manner as in Example 1 was charged, followed by the addition of 22 g of methanol and 104 g of water. The resulting mixture was heated to 70° C. to completely dissolve the crystals in the solvent, whereby a solution having a methanol content of 15 wt. % in terms of the concentration in the whole solution was prepared. This vessel (three-necked flask) having the solution therein was equipped with an agitating blade, thermometer and the like, and then dipped in a water bath of 25° C. to cool the solution. When the temperature of the solution became 28° C., 0.4 g of A-type crystals was added or implanted as seed crystals. After the crystals were aged for 2 hours in the water bath of 25° C., the resulting crystals were collected by filtration.

As a result of measuring the diffracted X-rays of the wet crystals thus collected, by using CuKα rays in accordance with the powder X-ray diffraction method, they showed the specific peaks of diffracted X-rays at angles of diffraction (2θ, CuKα rays) of at least 6.0°, 24.8°, 8.2° and 16.5°, indicating that the resulting crystals were A-type crystals. The powder X-ray diffraction pattern at this time was the same as that of the wet A-type crystals shown in FIG. 3.

Figure 4:
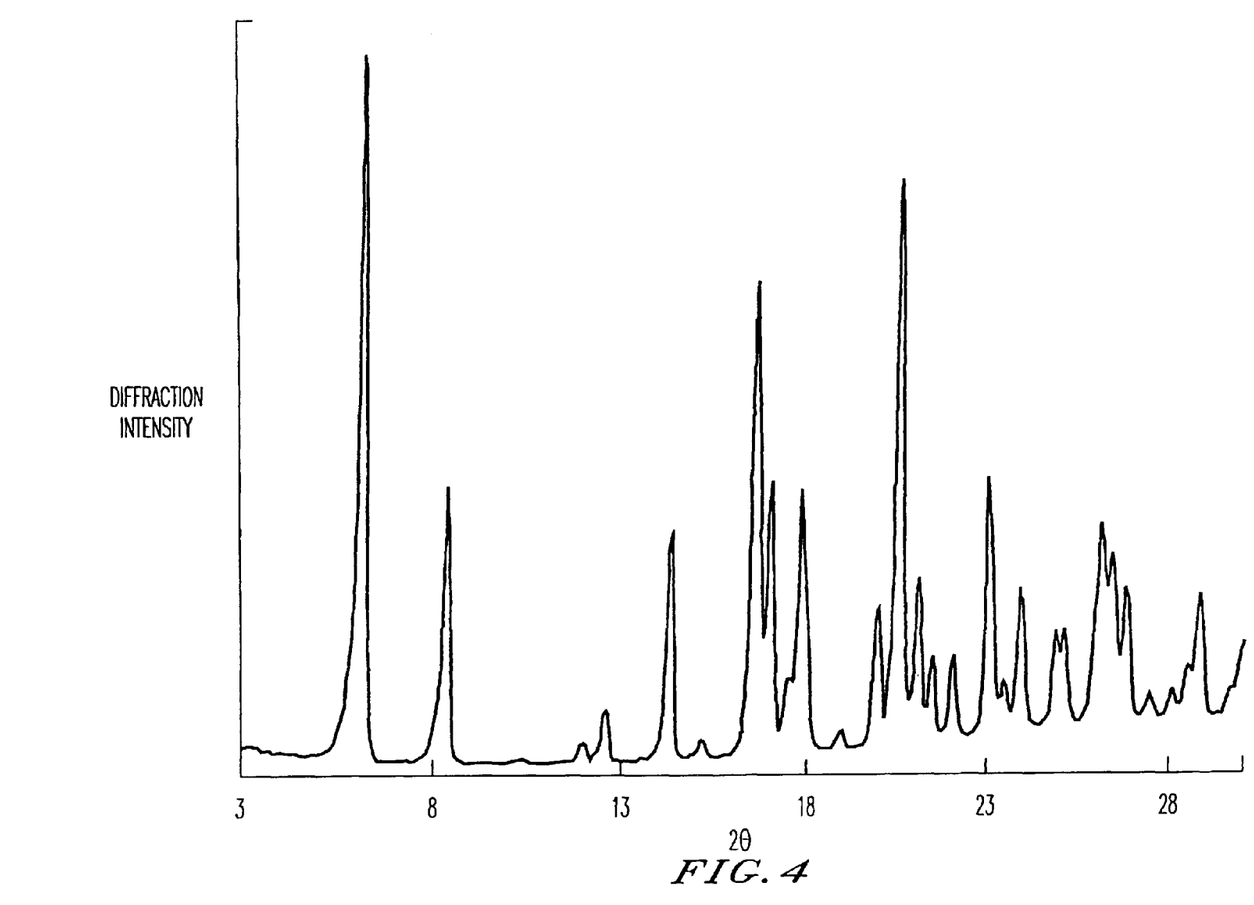
FIG. 4 shows a powder X-ray diffraction pattern of the dry A-type crystals (See Example 1).

Subsequently, the above-described wet crystals were dried at 50° C. under reduced pressure until the water content in the crystals became 4.5 wt. %. The powder X-ray diffraction pattern of the resulting crystals was identical to that of the dried A-type crystals as shown in FIG. 4, indicating that they were dry A-type crystals.

COMPARATIVE EXAMPLE 2

Spontaneous Nucleation at 25° C.

A three-necked flask containing therein the utterly same solution as in Example 5 was dipped in a water bath of 25° C. When the temperature of the solution became 25° C., nucleation occurred spontaneously. After the crystals were aged for 2 hours in the water bath of 25° C., the resulting crystals were collected by filtration.

As a result of measuring the diffracted X-rays of the wet crystals thus separated by filtering, by using CuKα rays in accordance with the powder X-ray diffraction method, the wet crystals thus collected showed the specific peaks of diffracted X-rays at angles of diffraction (2θ, CuKα rays) of at least 5.2°, 8.4°, 10.2° and 18.2°, indicating that the resulting crystals were B-type crystals.

EXAMPLE 6

Seeding at 22° C.

In the same manner as in Example 5, into a three-necked flask were charged 8.0 g of N-(3,3-dimethylbutyl)-APM, 24.2 g of methanol and 129.4 g of water. The resulting mixture was heated to 70° C. to completely dissolve the crystals in the solvent, whereby a solution having a methanol content of 15 wt. % in terms of the concentration in the whole solution was prepared. Subsequently, the three-necked flask having the solution therein was dipped in a water bath of 20° C. to cool the solution. When the temperature of the solution became 22° C., 0.16 g of A-type crystals was added as seed crystals. After the crystals were aged for 2 hours in the water bath of 20° C., the resulting crystals were collected by filtration.

As a result of measuring the diffracted X-rays of the wet crystals thus collected by filtering, by using CuKα rays in accordance with the powder X-ray diffraction method, it was found that the wet crystals were A-type crystals. Subsequently, the wet crystals were dried in the same manner as in Example 5, to obtain dry A-type crystals.

COMPARATIVE EXAMPLE 3

Spontaneous Nucleation at 21° C.

A three-necked flask containing therein the same solution as in Example 6 was dipped in a water bath of 20° C. When the temperature of the solution became 21° C., nucleation occurred spontaneously. After the crystals were aged for 2 hours in the water bath of 20° C., the resulting crystals were collected by filtration.

As a result of measuring the diffracted x-rays of the wet crystals thus separated by filtering, by using CuKα rays in accordance with the powder x-ray diffraction method, it was found that the wet crystals were b-type crystals, and it was tried in vain to confirm the existence of A-type crystals.

Industrial Applicability

According to the present invention, highly stable crystals of n-(3,3-dimethylbutyl)-APM, which is a high intensive sweetener, can be prepared conveniently and at a low cost, by carrying out crystallization while controlling the nucleation temperature and the composition of an N-(3,3-dimethylbutyl)-APM solution, or while using A-type crystals of N-(3,3-dimethylbutyl)-APM as seed crystals.

What is claimed is:

1. A method for preparing A-type crystals of N-[N-(3,3-dimethylbutyl)-L-α-aspartyl]-L-phenylalanine methyl ester, comprising:

crystallizing N-[N-(3,3-dimethylbutyl)-L-α-aspartyl]-L-phenylalanine methyl ester from a solution comprising N-[N-(3,3-dimethylbutyl)-L-α-aspartyl]-L-phenylalanine methyl ester and a solvent, to obtain A-type crystals of N-[N-(3,3-dimethylbutyl)-L-α-aspartyl]-L-phenylalanine methyl ester, wherein said solvent is selected from the group consisting of water and mixtures of water and a lower alcohol, wherein said crystallizing is carried out such that the temperature of said solution is maintained above 47° C. until onset of nucleation of said A-type N-[N-(3,3-dimethylbutyl)-L-α-aspartyl]-L-phenylalanine methyl ester.

2. The method of claim 1, wherein said solvent is a mixture of water and methanol.

3. The method of claim 1, wherein said methanol is present in said solvent in an amount of 15 wt. % or less, based on the total weight of said solvent.

4. The method of claim 1, wherein said solvent is water.

5. A method for preparing A-type crystals of N-[N-(3,3-dimethylbutyl)-L-α-aspartyl]-L-phenylalanine methyl ester, comprising:

crystallizing N-[N-3,3-dimethylbutyl)-L-α-aspartyl]-L-phenylalanine methyl ester from a solution comprising N-[N-(3,3-dimethylbutyl)-L-α-aspartyl]-L-phenylalanine methyl ester and a solvent, to obtain A-type crystals of N-[N-(3,3-dimethylbutyl)-L-α-aspartyl]-L-phenylalanine methyl ester, wherein said solvent is selected from the group consisting of water and mixtures of water and a lower alcohol, wherein said crystallizing is carried out in the presence of seed crystals of A-type N-[N-(3,3-dimethylbutyl)-L-α-aspartyl]-L-phenylalanine methyl ester.

6. The method of claim 5, wherein said solvent is a mixture of water and methanol.

7. The method of claim 6, wherein said methanol is present in said solvent in an amount of 15 wt. % or less, based on the total weight of said solvent.

8. The method of claim 5, wherein said solvent is water.

9. The method of claim 1, wherein said A-type crystals of N-[N-(3,3-dimethylbutyl)-L-α-aspartyl]-L-phenylalanine methyl ester exhibit a CuKα x-ray diffraction pattern having characteristic peaks expressed in degrees 2θ at 6.0°, 8.2°, 16.5°, and 24.8°.

10. The method of claim 1, wherein said A-type crystals of N-[N-(3,3-dimethylbutyl)-L-α-aspartyl]-L-phenylalanine methyl ester exhibit a CuKα x-ray diffraction pattern having characteristic peaks expressed in degrees 2θ at 6.0°, 8.2°, 16.5°, and 24.8°.

11. The method of claim 5, wherein said seed crystals of A-type crystals of N-[N-(3,3-dimethylbutyl)-L-α-aspartyl]-L-phenylalanine methyl ester exhibit a CuKα x-ray diffraction pattern having characteristic peaks expressed in degrees 20 at 6.0°, 8.2°, 16.5°, and 24.8°.

12. A method for preparing A-type crystals of N-[N-(3,3-dimethylbutyl)-L-α-aspartyl]-L-phenylalanine methyl ester, comprising:

crystallizing N— (N-(3,3-dimethylbutyl)-L-α-aspartyl]-L-phenylalanine methyl ester from a solution comprising N-[N-(3,3-dimethylbutyl)-L-α-aspartyl]-L-phenylalanine methyl ester and a solvent, to obtain A-type crystals of N-[N-(3,3-dimethylbutyl)-L-α-aspartyl]-L-phenylalanine methyl ester, wherein said solvent is selected from the group consisting of water and mixtures of water and a lower alcohol, wherein said crystallizing is carried out such that the temperature of said solution is maintained at 40° C. to 50° C. until onset of nucleation of said A-type N-[N-(3,3-dimethylbutyl)-L-α-aspartyl]-L-phenylalanine methyl ester.

13. The method of claim 12, wherein said solvent is a mixture of water and methanol.

14. The method of claim 13, wherein said methanol is present in said solvent in an amount of 15 wt. % or less, based on the total weight of said solvent.

15. The method of claim 12, wherein said solvent is water.

16. The method of claim 12, wherein said A-type crystals of N-[N-(3,3-dimethylbutyl)-L-α-aspartyl]-L-phenylalanine methyl ester exhibit a CuKα x-ray diffraction pattern having characteristic peaks expressed in degrees 2θ at 6.0°, 8.2°, 16.5°, and 24.8°.

* * * * *

UNITED STATES PATENT AND TRADEMARK OFFICE
CERTIFICATE OF CORRECTION

PATENT NO. : 6,914,151 B1
DATED : July 5, 2005
INVENTOR(S) : Shigeru Kawahara et al.

It is certified that error appears in the above-identified patent and that said Letters Patent is hereby corrected as shown below:

Column 9,
Line 38, "claim 1" should read -- claim 2 --.

Column 10,
Line 14, "claim 1" should read -- claim 5 --.

Signed and Sealed this

Eleventh Day of October, 2005

JON W. DUDAS
*Director of the United States Patent and Trademark Office*